United States Patent [19]

Hamdy

[11] Patent Number: 4,929,452

[45] Date of Patent: May 29, 1990

[54] METHOD FOR RAPIDLY FERMENTING ALCOHOLIC BEVERAGES

[75] Inventor: Mostafa K. Hamdy, Athens, Ga.

[73] Assignee: University of Georgia Research Foundation, Inc., Athens, Ga.

[21] Appl. No.: 370,839

[22] Filed: Jun. 22, 1989

Related U.S. Application Data

[63] Continuation of Ser. No. 103,049, Sep. 30, 1987, abandoned.

[51] Int. Cl.$^5$ .................. C12C 11/00; C12G 1/00; C12G 3/00
[52] U.S. Cl. .................. 426/11; 426/15; 426/16; 426/592; 426/29
[58] Field of Search .................. 426/592, 11, 15, 16, 426/29

[56] References Cited

U.S. PATENT DOCUMENTS 4,579,739 4/1986 Darbyshire et al. .................. 426/15
4,698,224 10/1987 Nakanishi et al. .................. 426/15

OTHER PUBLICATIONS

Jimenez et al., Appl. Environ. Microbiol., 54, 917–922 (1988).
Brown et al., Eur. J. Appl. Microbiol. Biotechnol., 16, 119–122 (1982).
Underkofler et al., "Industrial Fermentations", Chemical Publ. Co., Inc. N.Y., 1954, pp. 17–55, 196–245.

*Primary Examiner*—Marianne Cintins
*Attorney, Agent, or Firm*—Kilpatrick & Cody

[57] ABSTRACT

A method for the accelerated brewing of alcohol and alcoholic beverages including beer, wine, and spirits utilizing flavor producing strains of *S. cerevisiae* and/or other bacteria such as lactobacillus spp. and a high alcohol-tolerant strain of *S. cerevisiae*. Preferred strains of *S. cerevisiae* for the production of beer are ATCC Nos. 20866 and 20867.

In the preferred method, the fermentation is conducted in a bioreactor containing the flavor-producing strains and the high alcohol tolerant strain of *S. cerevisiae* immobilized on inert, high surface area supports, preferably porous organic or glass beads. The bioreactor significantly decreases the fermentation time necessary to produce a beverage containing a desired alcohol percentage. For example, beer can be processed in less than about 12 to 18 hours, wine in less than about 36 hours.

13 Claims, 2 Drawing Sheets and greatly increase the cost of both production and storage. Various processes have been tried to shorten the time required for fermentation. In almost all cases, however, such efforts result in deterioration of the aroma and flavor of the final product.

METHOD FOR RAPIDLY FERMENTING ALCOHOLIC BEVERAGES

This is a continuation of U.S. Ser. No. 103,049, entitled "Method for Rapidly Fermenting Alcoholic Beverages", filed Sept. 30, 1987, now abandoned, by Mostafa Kamal Hamdy.

FIELD OF THE INVENTION

The present invention relates in general to methods of making alcoholic beverages such as beer, wine, and spirits.

BACKGROUND OF THE INVENTION

While alcoholic fermentation can be expressed by a series of enzyme-catalyzed biochemical reactions, brewing and wine-making are ancient arts practiced centuries before the science of chemistry was born. The biochemistry of wine-making was demonstrated in 1856 by Louis Pasteur when he showed that wine is produced when the simple sugars in the fruit juices are fermented by yeast, *Saccharomyces cerevisiae*, to yield ethanol and carbon dioxide. Vinegar was produced when the yeast cultures were contaminated by other organisms.

Beer is made in a similar manner by the fermentation of the carbohydrates present in cereal grains such as barley. These carbohydrates, largely polysaccharides, are not degraded by the glycolytic enzymes in yeast cells, which can only act on disaccharides and monosaccharides. This problem is overcome by "malting" the barley. In malting, the cereal seeds are allowed to germinate until they form the appropriate enzymes required to break down the polysaccharides of the cell walls as well as the starch and other polysaccharide food reserves within the cells of the seeds. Germination is then stopped by controlled heating. The malt now contains enzymes such as alpha amylase and maltase that are capable of breaking down the starch to maltose, glucose and other simple sugars. In the next step, the brewer prepares the "wort" by mixing the malt with water and mashing. This allows the enzymes to break down the cereal polysaccharides into the simple sugars which are soluble in the liquid medium. The remaining cell matter is then separated and the liquid wort boiled with hops to provide flavor. The yeast cells are then added. In the presence of oxygen, the yeast cells are "activated", i.e. grow and reproduce very rapidly. No ethanol is formed until all of the oxygen is utilized. Under anaerobic conditions, the yeast ferments the sugars into ethanol and carbon dioxide. This fermentation process is controlled in part by the concentration of the ethanol formed, by the pH, and by the amount of sugar present. After the fermentation has been stopped, the cells are removed and the raw beer is ready for final processing (adjustment of the amount of "head", $CO_2$ concentration, concentration of flavorings).

Cordials and spirits are initially prepared in the same way as beer, by fermentation of a cereal mash. The alcohol produced by fermentation is the: distilled to yield a product having an alcohol content of 30–50%. The only flavoring present in the final product, for example, rum, vodka or gin, are those volatile compounds which accompany the alcohol or which are added to the concentrated alcohol.

These methods require long fermentation times and large processing and storage equipment. As can be readily seen, these requirements restrict output capacity and greatly increase the cost of both production and storage. Various processes have been tried to shorten the time required for fermentation. In almost all cases, however, such efforts result in deterioration of the aroma and flavor of the final product.

It is therefore an object of the present invention to provide a process and means for preparing a rapidly fermented alcoholic beverage which possesses all of the desirable flavor characteristics of the beverage processed by conventional methods.

It is a further object of the present invention to provide a bioreactor containing yeast allowing fermentation at an enhanced rate at a higher percentage of alcohol than is presently possible.

It is another object of the present invention to provide yeast and bacterial strains for use in the bioreactor.

SUMMARY OF THE INVENTION

The present invention is a method and means for rapidly fermenting alcohol and alcoholic beverages, including beer, wine, cordials and spirits, typically within 18 to 36 hours.

The alcoholic beverage is prepared by contacting a fermentation mixture with at least one high alcohol-tolerant strain of *S. cerevisiae*, and at least one flavor producing organism, such as a yeast and/or a bacteria such as lactobacillus.

Examples of preferred organisms are *S. cerevisiae* strains having ATCC Nos. 20867 (a high alcohol-tolerant strain) and 20866 (a beer flavor producing strain) and a malo-lactic acid wine flavoring lactobacillus species, or a mixture thereof. A high alcohol-tolerant high sugar-tolerant strain, such as ATCC No. 20867, can survive and reproduce in media having concentrations of up to about 20% alcohol and 45% sugar, in contrast to conventional strains that can tolerate concentrations of up to only about 7 to 8% alcohol and 10 to 15% sugar. Other strains of known microorganisms can be used to impart flavor.

In the preferred embodiment of this invention, the rapid brewing of an alcoholic beverage is conducted by immobilizing the organisms on inert, high surface area supports which are suspended in a column to form a bioreactor and then flowing the fermentation mixture through the suspended supports. Preferred support materials are glass, or organic beads, although other materials may also be used. The composition of organisms, the column bed volume, the pH, the concentration of sugars and flavorings in the feedstock, and the flow rates are factors determining the time to process a beverage and its final characteristics.

In one form of the bioreactor, consisting of two serially connected columns, the flavor producing organisms are immobilized in a bed of porous organic or glass beads in one column and an alcohol tolerant strain of *S. cerevisiae* is similarly immobilized in the second column. The liquid feedstock is repeatedly fed through the serially connected columns until the desired flavoring is reached, then fed solely through the second column until fermentation is complete. The size and volume of the columns and relative quantities of flavor producing organisms to high alcohol-tolerance organisms may also be modified to yield complete fermentation on a single pass. The flow rate through the reactor has a significant effect on the rate and efficiency of fermentation. The slower the flow rate, in general, the higher the efficiency.

Alternatively, the two columns may be replaced with a single column or varied to process the feedstock along either a horizontal or vertical axis. A particularly preferred embodiment is constructed at a 15 to 20 degree angle from the horizontal axis with a plurality of $CO_2$ ports to provide a favorable environment for the immobilized cells which maximizes fermentation efficiency. The beverages may also be processed batchwise using the high alcohol-tolerant strain of S. cerevisiae.

DETAILED DESCRIPTION OF THE INVENTION

Figure 1:
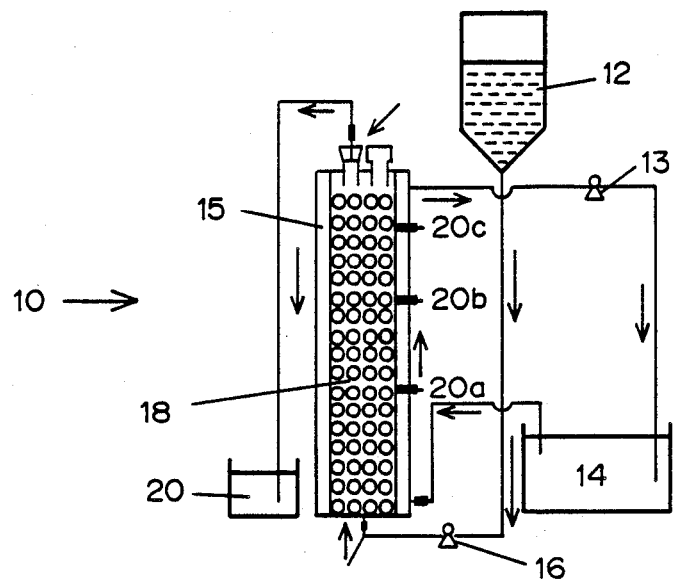
FIG. 1 is a schematic diagram of a bioreactor according to the present invention including organisms immobilized in a vertical reactor column.

The present invention is a method, and bioreactors for use in the method, for rapid fermentation of alcohol and alcoholic beverages. Rapid fermentation of a fermentation mixture is accomplished in the presence of a mixture of at least one flavor producing strain of S. cerevisiae (for beer) and/or lactobacillus (for wine) or other bacteria and at least one high alcohol-tolerant strain of S. cerevisiae which produces alcohol at a rate of at least about 0.026 grams alcohol per hour per gram sugar per $10^{12}$ yeast cells, preferably immobilized on inert, high surface area substrates suspended in a bioreactor.

"Alcoholic beverages" includes beverages made by fermentation of grains and fruit juices, such as beer, either "top" or "bottom" fermented varieties, (0.5 to 8% alcohol), wine (12 to 21% alcohol), cordials (21 to 30% alcohol), and spirits (30–50% alcohol). The substrates employed for the manufacture of the beverage according to the present process vary depending on the type of beverage to be produced. The feedstock for beer and spirits is a malt formed from a cereal mash. The feedstock for wine is usually crushed fruit or fruit juice. Alcohol for use in increasing the alcohol content of a beverage or for uses other than consumption can also be produced using the method of the present invention on a variety of organic subtrates. Alcoholic malt beverages with normal alcohol content, but much lower in caloric content, which are made by adding extra enzymes during mashing to breakdown malt substances, can also be prepared using the process of the present invention.

The ratio of sugar to liquid for producing beer is 2.2 lbs. sugar and 1.1 lbs. malt in 16.2 l. yields 3 to 4% alcohol. For wine, one must have at least a ratio of two to one sugar to final alcohol concentration. The ratios are based on the conversion of 100 g sugar to 50 g alcohol.

Wine is prepared according to the present invention using fruit crushed and filtered to form the feedstock solution. Skins and seeds are removed prior to crushing according to the desired characteristics of the final product (i.e., white versus red wine). Variables in the final product result from differences in sugar content, source of the fruit, the fermenting organisms, the pH, the time of fermentation, etc. Once the wine reaches about 12-20% alcohol, primary fermentation is complete and the wine can be aged or further processed according to taste.

Other alcoholic beverages are prepared in a fashion initially similar to beer, by the fermentation of a mash formed from cereal grains. These include whiskey, scotch whiskey, rum, gin and vodka, as well as cordials. The final alcoholic content of these beverages is higher than for wine and beer, around 21 to 30% for cordials and greater than 30%, usually greater than 45%, for spirits. The alcohol obtained by fermentation according to the present invention is distilled to produce concentrations of greater than about 20%. The alcoholic beverages produced by distillation, with the exception of whiskey and cordials, do not contain any flavorings other than volatiles associated with the alcohol. Whiskey is traditionally flavored by storage in charred oak vats. Cordials can contain other flavorings such as fruit syrups.

The alcoholic content of all of these beverages can be increased by addition of distilled alcohol to the fermented product or by increasing the amount of sugar present in the fermentation mixture.

When used here, the words "primary fermentation" mean a process of fermentation which is initiated by the addition of yeast to a wort or fruit juice. "Secondary fermentation" indicates the process of storage of unmatured malt beverage or wine following the primary fermentation until it acquires the characteristic aroma and flavor of the matured beverage. When the secondary fermentation is carried out at low temperature under pressure, the physico-chemical stability of the beverage is increased and the dissolution of carbon dioxide into the beverage is enhanced.

The present invention encompasses mutant strains of S. cerevisiae having high tolerance to sugar and alcohol. High sugar concentrations, required for high alcohol production, can cause cell death or plasmosis. Yeast normally cannot tolerate alcohol in concentrations in excess of about 7 to 8%. High alcohol tolerance is defined as the ability to survive and reproduce in a media having a higher concentration of alcohol. Normal yeast strains can tolerate about 10 to 15% sugar. An alcohol tolerant, sugar tolerant yeast strain was deposited with the American Type Culture Collection, Rockville, MD, on Sept. 17, 1987 and assigned ATCC No. 20867. This yeast can tolerate concentration of up to about 20% alcohol. Sugar tolerant yeast can tolerate concentrations in excess of 20%, up to about 45% with the preferred strain.

Known S. cerevisiae yeast strains may be utilized to develop mutants which are capable of growing in a high sugar, high alcohol-containing medium, employing basic techniques relating to the mutation of microorganisms known to those skilled in the art. A recent review is found in U.S. Pat. No. 4,029,549 and the references contained therein. Typically, the organisms are exposed to a mutating agent and then screened for the features which are desired, for example, growth in a high-alcohol, high sugar-containing mixture.

Other strains of organisms which constitute part of the present invention include flavor producing S. cerevisiae strains, for example, the beer-flavoring strain deposited with the ATCC on Sept. 17, 1987, and assigned ATCC No. 20866.

The microorganisms are maintained in culture using methods and materials available to those skilled in the art.

By fermenting a malt liquor mixture or fruit juice mixture in the presence of a flavor producing strain of *Saccharomyces cerevisiae* or other bacteria such as lactobacillus and a high alcohol-tolerant mutant strain of *Saccharomyces cerevisiae*, the rate of fermentation can be accelerated to complete fermentation of beer or wine within about 18 to 36 hours.

In the preferred embodiment of the process the microorganisms are immobilized in and on rigid inert supports having high surface area. Preferred supports are glass or organic porous beads, although other materials such as ceramics and alumina (only for use in production of fuel alcohol), and other types of supports, may be utilized. Caution must be exercised to avoid supports that might determinally affect flavor. Preferred average bead diameter is 0.4 to 0.45 cm, although beads having a diameter between 0.25 and 0.6 cm are acceptable. The supports should have sufficient surface area for attachment of at least $10^9$ to $10^{11}$ cells/g support.

In the most preferred embodiment of the present invention, the immobilized organisms are suspended in a bioreactor of a length and diameter proportional to the amount of feedstock to be fermented. The system can be designed to ferment the feedstock to yield a desired concentration of alcohol on a single or on multiple passes through the reactor. The reactor preferably consists of one or more hollow cylindrical "columns". In one embodiment, the flavor producing organisms are placed in a first column and the high alcohol-tolerant yeast placed in a second column, so that the feedstock can be fed into either or both columns to obtain the desired flavoring while not killing the flavor producing organisms through exposure to high concentrations of alcohol.

Batch Processing of an Alcoholic Beverage Using High Alcohol Tolerant Yeast Strains Although the maximum rate of fermentation is obtained using the immobilized organisms, the mutant strains of the present invention allow for rapid fermentation of alcohol or an alcoholic beverage in a batch process without immobilization of the organisms.

In one embodiment, a liquid fermentation mixture and both a flavor producing organism (or mixture of organisms) and a high alcohol-tolerant strain of *S. cerevisiae* such as ATCC 20867 are mixed in a fermentation vessel. The mixture is heated for up to about 2 hours, at a temperature of between 25° C. and 40° C., preferably about 30° C., while an oxygen-containing gas is bubbled through the mixture to activate the culture. The fermentation temperature in the fermentation vessel is then lowered to between about 24° and 35° C., preferably about 28° C., and maintained at the lower temperature level for between about 4 to 36 additional hours to complete the fermentation. The fermented beverage is then withdrawn from the fermentation vessel and the spent yeast separated from the beverage.

General batch processing is further described by the following non-limiting "recipe".

1.1 pounds of heated liquid malt extract was poured into a 5 gallon vat fermenter. 2.5 pounds sugar and about ½ tbsp. salt were added to the malt extract in the fermenter. The fermenter was then filled with about 16.2 liters freshly distilled hot water.

About equal amounts, approximately 0.5 liter, of a flavor-producing yeast strain and high alcohol-tolerant yeast strain were added to a concentration effective to permit rapid fermentation, about $10^8$ cfu/ml. The fermentation was allowed to proceed at about 30° C. (the useful temperature range is between about 25° and 40° C.), for a time between about 1 and 2 hours, bubbling oxygen gas or a stream of air in a constant stream through the liquor to activate the culture. The temperature in the fermenter was then lowered to about 28° C., (the acceptable range is between 24° and 35° C.), and maintained at this level for a period of between about 4 and 18 hours, preferably about 3-17 hours for fermentation of beer.

After a period of about 18 hours (the range is between about 12 and 36 hours or when the fermentation is complete), the solution solids were allowed to settle out and the malt beverage, a completely fermented beer, was withdrawn from the top.

For wine, one would use approximately ⅓ alcohol-tolerant yeast, ⅓ lactobacilli, and ⅓ flavoring yeast. For beer, in general, the alcohol-tolerant yeast and flavoring yeast are added in about equal amounts. If higher alcohol content is desired, more sugar can be added at intervals during the fermentation process.

A procedure for preparing wort and fermenting it according to the method of the present invention to produce beer has the following steps:

Placing the malt liquor fermentation mixture in a fermentation vessel; heating the mixture for between about 1 and 2 hours at a temperature of between 38° and 40° C.; adding one half of a total amount of hops to the fermentation vessel; heating the hop-fermentation mixture at a temperature of between about 50° and 55° C. for an additional 0.5 to 1 hours; elevating the fermentation temperature of the liquor to between about 60° and 65° C. and holding the temperature at that level for between about 30 and 35 more minutes, then adding the other half of the hops; increasing the vessel temperature to between about 70° and 75° C., holding this temperature for between about 25 and 35 more minutes; and finally increasing the vessel temperature to between about 80° and 90° C., boiling for between about 30 and 35 minutes and then rapidly cooling the mixture to between about 25° and 35° C.

Adding to the fermentation vessel water and a mixture of malt flavor producing strain of *S. cerevisiae* and at least one high alcohol-tolerant sugar-tolerant strain of *S. cerevisiae* capable of accelerating the fermentation of the malt liquor; heating the mixture for between 30 and 35 minutes at a temperature of between 24° and 30° C. while bubbling an oxygen-containing gas therethrough; lowering the temperature in the fermentation vessel to between about 26° and 28° C., and maintaining the lower temperature level for between about 24 to 48 hours to complete the fermentation.

The beverage is then withdrawn from the fermentation vessel while the spent yeast is separated out.

The alcoholic malt beverage produced according to this invention can be filtered, clarified, salts and/or $CO_2$ added and bottled for distribution according to known procedures in the art.

Figure 2:
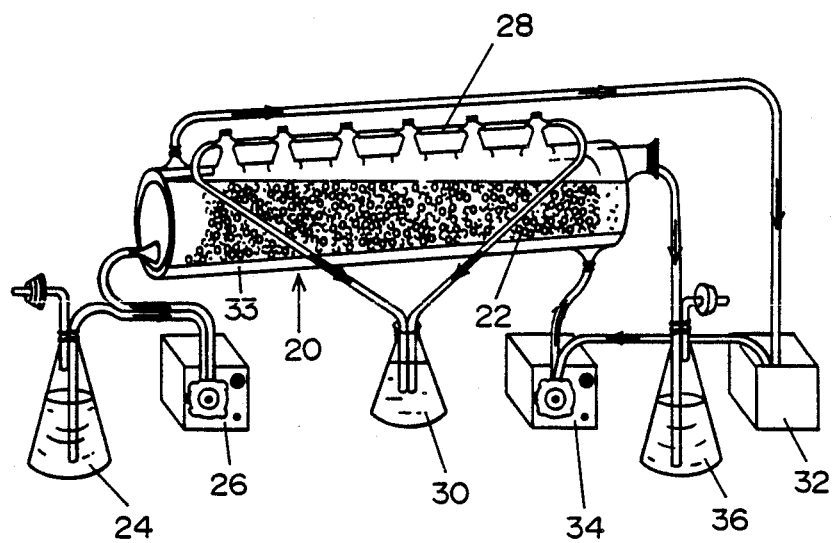
FIG. 2 is an angled horizontal bioreactor system according to the present invention including organisms immobilized on inert supports, feedstock, pumps, and a $CO_2$ trap.
Figure 3:
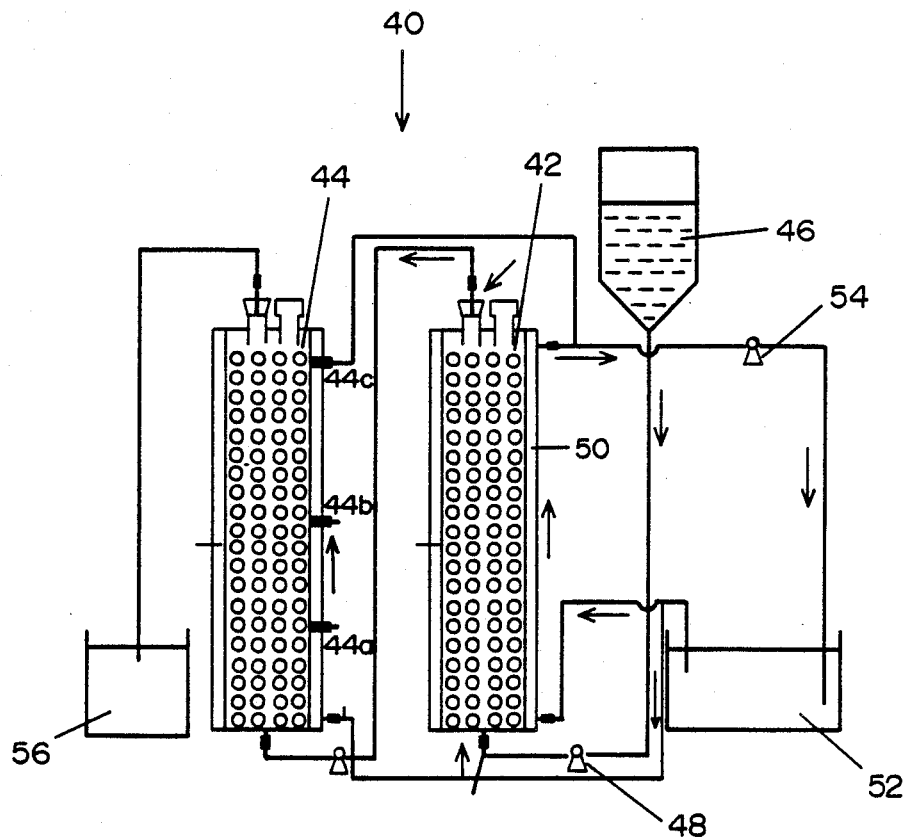
FIG. 3 is a schematic of a two column bioreactor according to the present invention.

A more preferred embodiment of the above process utilizes immobilized strains of *S. cerevisiae* on high surface area supports in a bioreactor, as shown in FIGS. 1, 2, and 3. As depicted, the fermentation mixture is passed through the bioreactor containing flavor producing microorganisms and the high alcohol tolerant strain of *S. cerevisiae* immobilized in beds of porous organic or glass beads until the primary fermentation is complete.

Processing Of An Alcoholic Beverage In A Bioreactor Containing Microorganisms Immobilized On High Surface Area Supports.

The purpose of immobilizing the organisms in the bioreactor is to further accelerate fermentation by processing the beverage at a continuous rate without the addition of new yeast. In a preferred embodiment for processing beer, yeast cells of a malt flavor producing strain of a bacteria or *Saccharomyces cerevisiae*, are immobilized on organic or glass supports having a high surface area in a first column or section of the bioreactor. A second column contains one or more of the high alcohol-tolerant *S. cerevisiae* strains also immobilized on organic or glass supports. The feedstock is fed into the bioreactor and passed through the immobilized organisms. After reaching a desired percentage of alcohol, which may take up to about 36 hours, the fermented liquor is withdrawn, clarified, bottled, or further processed, as necessary.

A preferred method for yeast cell immobilization is based on the procedure described by Messing and Opperman, *Biotech and Bioengineer.* 23 1813 (1981). This method can also be applied to bacterial cells. The yeast cells are allowed to grow for 48 hours at 37° C. (stationary phase) in a flask of a malt-glucose broth placed inside a metabolic shaker. This broth contains g/l deionized water as follows: malt extract, 20.0; glucose, 10.0; sucrose, 5.0; tryptone, 1.5; peptone, 1.5; $K_2HPO_4$, 1.0; $NH_4Cl$, 1.5, and $NaCl$, 1.0.

The yeast cells are then harvested by centrifugation, washed three times with sterile 0.05 M citrate-phosphate buffer (pH 3.5) and resuspended in the same buffer. The desired volume of cell suspension containing $10^9$ to $10^{11}$ cells/ml buffer is mixed with a known weight of sterile beads and incubated at 37° C. for 2 hr in a reciprocal metabolic shaker at a frequency of 75 rotations/min. The non-immobilized cells are poured off and the beads washed three times with citrate-phosphate buffer. The total number of immobilized cells per gram of beads is determined using both indirect and direct procedures. The former consists of counting the yeast cells in an appropriate dilution of supernatent following immobilization using a hemocytometer (Levy and Levy-Hausser corpuscle counting chamber, Hausser Sci., Philadelphia, Pennsylvania). The difference between the original number of yeast cells and that in the supernate (non-immobilized cells) is the number of immobilized cells per gram of beads. In the direct procedure, the beads are subjected to vigorous washing in saline solution. The total number of cells in nine 100 ml saline solution washes is determined using a hemocytometer as indicated above.

Factors affecting yeast immobilization include incubation time; pH; media; substrate form, composition and size; and amount of sugar.

The preferred supports are porous beads having a particle size between about 0.25 and 6 cm in diameter, preferably between 0.4 and 0.45 cm, formed of a material such as glass, an organic, a ceramic or alumina (for fuel alcohol production only). Examples of organics are carrageenan, agar, and alginates. Organic plastics are also useful. The supports should have internal pore diameters in the range of 5.0 to 12 microns. Other materials and support forms may be used, although maintaining adequate surface area for attachment of the cells and minimizing shear caused by the combination of the flow of the fermentation mixture and the evolution of $CO_2$ in the bioreactor are major considerations in the design of acceptable materials.

Regeneration of the glass or organic support is conducted by sterilization in an autoclave followed by washing with deionized water. Other sterilization methods such as gamma irradiation, 70% ethanol, and ethylene oxide could also be used.

The construction and processing of alcoholic beverage in bioreactors is further described by the following non-limiting examples.

EXAMPLE 1:

Rapid Fermentation of Beer in a Single Vertical Column Bioreactor.

Preparation of Immobilized Organisms:

134 grams of sterile channeled porous organic beads of an average diameter ranging from 0.4 to 0.45 cm with internal pore diameters of 5.0 to 12 microns were treated with 1 to 5 g of active stationary phase cells of *Saccharomyces cerevisiae* strain 177 at a pH of 5. The yeast cells ($10^9$–$10^{11}$ cells/g beads) were immobilized onto carrageenan beads (obtained from Fisher Scientific, Atlanta, Georgia), by incubation at 37° C. for 2 hours in a metabolic shaker.

Fermentation:

A feedstock for making dark beer containing one pound of malt extract; 2.5 pounds of sugar; 2–3 grams of salt; and 4.5 gallons of hot double distilled water was fed into a bioreactor column 10 (45 cm height, 7.0 cm I.D.) shown schematically in FIG. 1. The temperature of the circulating feedstock 12 was externally controlled between about 25° and 32° C. by means of a pump 13 circulating water via a water bath 14 to the column jacket 15. The pH of the feedstock was maintained at between about 4.5 and 5.5.

The malt containing feedstock 12 was fed via a peristatic pump 16 at a constant flow rate of 85 ml/hour into the immobilized organisms-substrate 18. Reaction product samples were withdrawn from three exit ports 20a, 20b, 20c (equal to 15, 30 and 45 cm in height). At the conclusion of the fermentation, exit port 20a showed a 73 to 71% yield of beer product having an alcoholic content of 2 or more % ethanol; the exit port 20b showed an 86% yield of beer product having an alcoholic content of 3 or more % ethanol and exit port 20c showed a 96% yield of product and 3.5–4% or more ethanol. The final product is collected at container 20. This was operated for eight months and demonstrates the particular usefullness of the bioreactor—that is, it can be turned on and off at will and maintained for an indefinite period of time.

Varying the flow rate allows one to improve the efficiency of the system. In general, decreasing the flow rate increases the efficiency. Decreasing the flow rate also provides a means for minimizing shear within the bioreactor and thereby decreases the number of organisms dislodged from the supports thereby allowing for long term operation of the system.

EXAMPLE 2:

Rapid fermentation of beer in a Horizontal Bioreactor:

In an alternative embodiment of the single column bioreactor which is positioned vertically, a column 22 can be constructed with the immobilized organisms support particles 22 positioned to form a 15 to 20 degree angle to the horizontal axis, as depicted in FIG. 2. Feedstock is fed from container 24 via a peristaltic pump 26 to the bioreactor column 20 where it is contacted with the immobilized high alcohol-tolerant yeast and flavor producing organisms 22. $CO_2$ gas is evolved and collected via port connections 28 in a container 30. The temperature of the feedstock 24 is maintained by a waterbath 32 connected to the bioreactor column jacket 33 through a second peristaltic pump 34. The fermented product is collected at the effluent container 36.

The purpose of constructing the bioreactor containing support particles arranged to form an approximately 15-20 degree angle to the horizontal axis is that, in combination with the multiple ports for removal of $CO_2$, shear within the column is decreased and an efficiency of about 94-96% can be achieved. The trapped $CO_2$ can also be utilized to carbonate the fermented beverage or other beverages. Other angles and arrangements can be utilized, depending on the feedstock, reactor geometry, flow rate, and nature of supports.

Although depicted as completing the reaction in a single pass through the bioreactor 20, the system could easily be altered to provide for multiple passes of the feedstock through the immobilized organisms.

EXAMPLE 3:

Rapid fermentation of beer in a two column bioreactor.

A bioreactor 40 consisting of two jacketed glass columns 42 and 44 was used to ferment beer. A schematic diagram of the various components of the bioreactor 40 is shown in FIG. 3.

The first column 42 has a height of 31.0 cm and 3.3 cm inside diameter. The second column has a height of 45.0 cm and 7.0 cm inside diameter. The second column has three ports 44a, 44b, 44c, one at 15, 30, and 45 cm height. The glass column reactors were sterilized separately using 70 (v/w)% ethanol for 24 hr before use. The other components were sterilized at 121° C. for 15 min.

The columns 42, 44 were packed with yeast cells immobilized onto beads ($10^9$ to $10^{11}$ cells/g 0.4 to 0.45 cm diameter beads). The feed stock 46 was continuously fed to the column 42 by a peristaltic pump 48 at a desired flow rate, for example, 20 to 30 ml/min. The temperature of the bioreactor 40 was kept constant by continuously circulating water via a pump 54 to the column jacket 50 from a water bath 52 kept at a desired temperature. The operation of the bioreactor reaches a steady state when the ethanol and residual sugar concentration leveled off, as evidenced by assaying three successive samples at 30 min intervals. The final product was collected in container 56.

Both flow and dilution rates inversely affect the percent alcohol and percent yield due to the increased residence time of feedstock in the bioreactor. The yield was doubled when the feedstock flow rate was decreased to 25% of the initial value.

While the above examples illustrate the process by reference to a small batch reactor and quantities of up to 100 gallons per batch, it is clearly within the scope of the present invention to scale up the methods and equipment to 1000, 5000 and 10,000 gallon or larger vat capacity equipment, while continuing to process the alcoholic beverage in a comparable span of less than 24 to 36 hours of total elapsed brewing time. The amounts of all components are scaled up proportionately in accordance with the volume of the reactors, type of feedstock and final product which is desired.

Modifications and variations of the present invention, a process and means for rapid fermentation of alcohol and alcoholic beverages including beer, wine, and spirits, will be apparent to those skilled in the art form the foregoing detailed description. Such modifications and variations are intended to be included within the scope of the following claims.

I claim:

1. A process for producing an alcohol solution comprising fermenting a sugar mixture with a strain of *Saccharomyces cerevisiae* which can tolerate alcohol concentrations of greater than 12% and sugar concentrations of greater than 20%, wherein said strain of *S. cerevisiae* rapidly ferments sugar substrates, producing alcohol at a rate of at least about 0.026 grams alcohol per hour per gram sugar per $10^{12}$ yeast cells.

2. The process of claim 1 wherein the alcohol-tolerant, sugar-tolerant strain of *S. cerevisiae* is immobilized on an inert high surface area support having a binding capacity of greater than about $10^9$ cells/gm of support.

3. The process of claim 1 for producing an alcoholic beverage further comprising fermenting the sugar mixture with flavor producing microorganisms, wherein the flavor producing microorganisms and the alcohol-tolerant, sugar-tolerant strain are present in about equal amounts.

4. The process of claim 1 for producing an alcoholic beverage further comprising fermenting the sugar mixture with flavor producing microorganisms, wherein the flavor producing microorganisms are an approximately equal mixture of lactobacillus and *Saccharomyces cerevisiae*.

5. The process of claim 1 further comprising providing beer flavoring organisms and substrates selected from the group consisting of malt, barley, and hops and fermenting the substrates to produce beer.

6. The process of claim 1 further comprising providing wine flavoring organisms and sugar containing substrates to produce wine.

7. The process of claim 1 further comprising providing additional microorganisms selected from the group consisting of *S. cerevisiae* ATCC 20866, *S. cerevisiae* ATCC 20867, lactobacillus spp., and mixtures thereof.

8. The process of claim 5 comprising:
   (a) mixing in a fermentation vessel a sugar fermentation substrate and a mixture of at least one flavor producing microorganism and a strain of *S. cerevisiae* which can tolerate alcohol concentrations of greater than 12% and sugar concentrations of greater than 20%, wherein said strain of *S. cerevisae* rapidly ferments sugar substrates, producing alcohol at a rate of at least about 0.026 grams alcohol per hour per gram sugar per $10^{12}$ yeast cells;
   (b) heating the mixture for between 0.5 and 1 hour at a temperature of between 50° and 60° C. while bubbling an oxygen-containing gas therethrough;
   (c) lowering the fermentation temperature in the fermentation vessel to between about 25° and 35° C. and maintaining the lower temperature level until fermentation is complete; and
   (d) separating the alcohol solution from the microorganisms in the fermentation vessel.

9. The method of claim 2 wherein the microorganisms are immobilized on porous, inert beads.

10. The method of claim 2 wherein the sugar mixture is passed through a bioreactor having at least one portion containing a suspension of flavor producing microorganisms immobilized on inert surface area supports and a second portion having the high alcohol tolerant, sugar-tolerant strain of *S. cerevisiae* immobilized on the inert, high high surface area supports.

11. The method of claim 10 further comprising constructing the bioreactor from a plurality of columns.

12. The method of claim 11 wherein the alcohol-tolerant, sugar-tolerant microorganisms and the flavor producing microorganisms are immobilized in separate columns.

13. The method of claim 9 wherein the supports are porous beads having an average diameter of between about 0.25 and 0.6 cm.

* * * * *